(12) United States Patent
Hoyos et al.

(10) Patent No.: US 11,054,243 B2
(45) Date of Patent: Jul. 6, 2021

(54) ELECTRONIC DEVICE FOR AUTOMATIC CALIBRATION OF SWEPT-SOURCE OPTICAL COHERENCE TOMOGRAPHY SYSTEMS

(71) Applicant: The Texas A&M University System, College Station, TX (US)

(72) Inventors: Sebastian Hoyos, Bryan, TX (US); Oscar Joseu Pacheco Barajas, Bryan, TX (US); Amir Tofighi Zavareh, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 45 days.

(21) Appl. No.: 16/497,036

(22) PCT Filed: Apr. 25, 2018

(86) PCT No.: PCT/US2018/029423
§ 371 (c)(1),
(2) Date: Sep. 24, 2019

(87) PCT Pub. No.: WO2018/200712
PCT Pub. Date: Nov. 1, 2018

(65) Prior Publication Data
US 2020/0378744 A1    Dec. 3, 2020

Related U.S. Application Data

(60) Provisional application No. 62/490,098, filed on Apr. 26, 2017.

(51) Int. Cl.
*G01B 9/02* (2006.01)
*A61B 5/00* (2006.01)
*G01N 21/47* (2006.01)

(52) U.S. Cl.
CPC ........ *G01B 9/02069* (2013.01); *A61B 5/0066* (2013.01); *A61B 5/725* (2013.01);
(Continued)

(58) Field of Classification Search
CPC ............ G01B 9/02069; G01B 9/02004; G01B 9/02083; G01B 9/02091; A61B 5/0066;
(Continued)

(56) References Cited

U.S. PATENT DOCUMENTS

2008/0212075 A1    9/2008  Paulus et al.
2011/0216325 A1    9/2011  Schmitt
(Continued)

OTHER PUBLICATIONS

A. T. Zavareh et al., "A novel continuous time ternary encoding based SS-OCT calibration," 2016 IEEE Biomedical Circuits and Systems Conference (BioCAS), Shanghai, 2016, pp. 5-8, doi: 10.1109/BioCAS.2016.7833711. (Year: 2016).*
(Continued)

*Primary Examiner* — Dominic J Bologna
(74) *Attorney, Agent, or Firm* — Conley Rose, P.C.

(57) ABSTRACT

A circuit for generating a swept source optical coherence tomography (SS-OCT) imaging calibration clock. The circuit comprises a first photodetector configured to convert an SS-OCT optical calibration signal to an SS-OCT electrical calibration signal, a first analog-to-digital converter (ADC) coupled to the first photodetector and configured to convert the SS-OCT electrical calibration signal to a sequence of SS-OCT calibration signal digital values, a processing unit coupled to the first ADC that, when initiated, is configured to demodulate the sequence of SS-OCT calibration signal digital values to obtain a sequence of SS-OCT wave number digital values, where each SS-OCT wave number digital value corresponds to one of the SS-OCT calibration signal digital values, and a level crossing sampler that is configured to track a wave number associated with the SS-OCT optical (Continued)

calibration signal and to generate an SS-OCT calibration clock pulse.

20 Claims, 7 Drawing Sheets

(52) U.S. Cl.
CPC ........ *A61B 5/7257* (2013.01); *G01B 9/02004* (2013.01); *G01B 9/02083* (2013.01); *G01B 9/02091* (2013.01); *G01N 21/4785* (2013.01); *G01N 21/4795* (2013.01); *G01N 2201/127* (2013.01)

(58) Field of Classification Search
CPC .. A61B 5/725; A61B 5/7257; G01N 21/4785; G01N 21/4795; G01N 21/38; G01N 2201/127
See application file for complete search history.

(56) References Cited

U.S. PATENT DOCUMENTS

| | | |
|---|---|---|
| 2012/0013914 A1 | 1/2012 | Kemp et al. |
| 2013/0060131 A1 | 3/2013 | Oghalai et al. |
| 2013/0182259 A1 | 7/2013 | Brezinski et al. |
| 2016/0161466 A1* | 6/2016 | Kuan Germano .......................... G01R 33/1269 702/19 |

OTHER PUBLICATIONS

Zavareh, Amir Tofighi, Oscar Barajas, and Sebastian Hoyos. "An efficient estimation algorithm for the calibration of low-cost SS-OCT systems." 2017 IEEE 14th International Symposium on Biomedical Imaging (ISBI 2017). IEEE, 2017. (Year: 2017).*

Barajas, Oscar, Amir Tofighi Zavareh, and Sebastian Hoyos. "Towards an on-chip signal processing solution for the online calibration of SS-OCT systems." 2017 IEEE International Symposium on Circuits and Systems (ISCAS). IEEE, 2017. (Year: 2017).*

Pacheco Barajas, Oscar Joseu (2017). Highly Efficient Spectral Calibration Methods for Swept-Source Optical Coherence Tomography. Master's thesis, Texas A & M University. Available electronically from http : //hdl .handle .net/1969 .1 /166112. (Year: 2017).*

Ehsan Azimi, Bin Liu, Mark E. Brezinski, "Real-time and high-performance calibration method for high-speed swept-source optical coherence tomography," J. Biomed. Opt. 15(1) 016005 (Jan. 1, 2010) https://doi.org/10.1117/1.3285660 (Year: 2010).*

Manapuram, Ravi Kiran, Venu Gopal Reddy Manne, and Kirill V. Larin. "Phase-sensitive swept source optical coherence tomography for imaging and quantifying of microbubbles in clear and scattering media." Journal of Applied Physics 105.10 (2009): 102040. (Year: 2009).*

PCT/US2018/029423 International Search Report and Written Opinion dated Jul. 6, 2018 (2238-09201) (14 p.).

* cited by examiner

ELECTRONIC DEVICE FOR AUTOMATIC CALIBRATION OF SWEPT-SOURCE OPTICAL COHERENCE TOMOGRAPHY SYSTEMS

CROSS-REFERENCE TO RELATED APPLICATIONS

This application is a 35 U.S.C. § 371 national stage application of PCT/US2018/029423 filed Apr. 25, 2018, entitled "Electronic Device for Automatic Calibration of Swept-Source Optical Coherence Tomography Systems," which claims benefit of U.S. provisional patent application Ser. No. 62/490,098 filed Apr. 26, 2017, and entitled "Electronic Device for Automatic Calibration of Swept-Source Optical Coherence Tomography Systems," each of which is hereby incorporated herein by reference in its entirety for all purposes.

STATEMENT REGARDING FEDERALLY SPONSORED RESEARCH OR DEVELOPMENT

Not applicable.

BACKGROUND

Optical Coherence Tomography (OCT) is an imaging technique that captures high resolution (e.g., micrometer-resolution) multi-dimensional (e.g., 2D or 3D) images from optical scattering objects (e.g., tissue) utilizing light. OCT has established itself as the de-facto biomedical imaging modality when low penetration and high resolution are desired. OCT is utilized in a wide array of applications and fields ranging from biomedical imaging to archeology. The rapid adoption and growth in OCT may be attributed at least in part to the ability to capture high-resolution cross sectional images without touching the eye in ophthalmic tomographic applications.

Basic OCT systems detect back scattered photons from a tissue using a two-beam interferometer. The light reflectivity information of the object under test is then extracted which enables image reconstruction. In one iteration of the technology, a time domain interferometer may be utilized with each depth corresponding to a different time delay. Each time delay is then measured by manually moving a reference arm so that depth information may be obtained at distinct times making the received data information time encoded. This OCT technique may be termed time domain OCT (TD-OCT). TD-OCT requires mechanical movement of the interferometer reference arm which may cause the system to suffer from lower ranging accuracy and speed when compared to modern Fourier transform based techniques. Fourier transform based techniques may be termed frequency domain OCT (FD-OCT). FD-OCT techniques utilize a less complex setup that need not rely on mechanical movement of the reference arm and may potentially achieve higher axial resolutions, faster data acquisition, and better sensitivity than typically can be provided by TD-OCT techniques. When utilizing FD-OCT techniques, spectral information of the interferogram is measured and light reflection coefficient information of the object under test is obtained via a Fourier transform performed on wavenumber space data. FD-OCT may be implemented in two ways: 1) spectral domain OCT (SD-OCT) using a broadband light source and a spectrometer with a multichannel analyzer and an InGaAs camera; and 2) swept source OCT (SS-OCT) using a narrow-band tunable swept-laser (light source) source and a single InGaAs photodetector.

When utilizing SS-OCT techniques, spectral information is acquired sequentially using a single InGaAs photodetector while rapidly sweeping the wavenumber, "k", of a narrow-band light source over a broad optical bandwidth producing two optical signals (e.g., by splitting the light emitted by the light source). One optical signal contains the tissue reflectivity information (interferometric signal, $I_D(t)$). The other optical signal is used for calibration purposes (calibrating signal, $I_{MZI}(t)$). The resulting calibrating signal may be described as a Gaussian damped sinusoid that non-uniformly sweeps across a spatial frequency band (e.g., across a range of k values) and may be made using different kinds of interferometers including but not limited to a Mach-Zehnder interferometer (MZI). It should be noted that if no calibration is performed, the wavenumber sweep profile affects the quality of the final image produced. That means when sampling the interferometric signal uniformly in time (no calibration), the generated images present considerable distortion because the reflectivity information of the object under test is a function of wavenumber "k", not time. In order to correct for this distortion, calibration may be performed.

SUMMARY

In an embodiment, a circuit for generating a swept source optical coherence tomography (SS-OCT) imaging calibration clock is disclosed. The circuit comprises a first photodetector configured to convert an SS-OCT optical calibration signal to an SS-OCT electrical calibration signal and a first analog-to-digital converter (ADC) coupled to the first photodetector and configured to convert the SS-OCT electrical calibration signal to a sequence of SS-OCT calibration signal digital values. The circuit further comprises a processing unit coupled to the first ADC that, when initiated, is configured to demodulate the sequence of SS-OCT calibration signal digital values to obtain a sequence of SS-OCT wave number digital values, where each SS-OCT wave number digital value corresponds to one of the SS-OCT calibration signal digital values and a level crossing sampler that is configured to track a wave number associated with the SS-OCT optical calibration signal and to generate an SS-OCT calibration clock pulse, whereby an SS-OCT interferometric optical signal is sampled based on the SS-OCT calibration pulse.

In another embodiment, a method of generating a swept source optical coherence tomography (SS-OCT) imaging calibration clock is disclosed. The method comprises converting an SS-OCT optical calibration signal by a photodetector to an SS-OCT electrical calibration signal and converting the SS-OCT electrical calibration signal by an analog-to-digital converter (ADC) to a sequence of SS-OCT calibration signal digital values. The method further comprises demodulating the sequence of SS-OCT calibration digital values by a processing unit to obtain a sequence of SS-OCT wave number digital values, where each SS-OCT wave number digital value corresponds to one of the SS-OCT calibration signal digital values and, in response to the SS-OCT wave number digital value matching one of a plurality of predefined SS-OCT wave number digital values, generating an SS-OCT calibration clock pulse, whereby an SS-OCT interferometric optical signal is sampled based on the SS-OCT calibration clock pulse.

In yet another embodiment, a circuit for generating a swept source optical coherence tomography (SS-OCT) imaging calibration clock is disclosed. The circuit comprises a first photodetector configured to convert an SS-OCT optical calibration signal to an SS-OCT electrical calibration signal, a first analog-to-digital converter (ADC) coupled to the first photodetector and configured to convert the SS-OCT electrical calibration signal to a sequence of SS-OCT calibration signal digital values, a processing unit coupled to the first ADC that, when initiated, is configured to demodulate the sequence of SS-OCT calibration signal digital values to obtain a sequence of SS-OCT wave number digital values, where each SS-OCT wave number digital value corresponds to one of the SS-OCT calibration signal digital values, and a level crossing sampler that is configured to track a wave number associated with the SS-OCT optical calibration signal and to generate an SS-OCT calibration clock pulse. The circuit further comprises a second photodetector configured to convert an SS-OCT optical interferometric signal to an SS-OCT electrical interferometric signal and a second ADC coupled to the second photodetector and coupled to receive the SS-OCT calibration clock pulse and configured to sample the SS-OCT electrical interferometric signal in response to the SS-OCT calibration clock pulse and to convert the sample to a SS-OCT interferometric signal digital value, where the processing unit is further configured to process a plurality of SS-OCT interferometric signal digital values to a light reflection coefficient value associated with a point on an imaging target.

These and other features will be more clearly understood from the following detailed description taken in conjunction with the accompanying drawings and claims.

BRIEF DESCRIPTION OF THE DRAWINGS

For a detailed description of various examples, reference will now be made to the accompanying drawings in which.

NOTATION AND NOMENCLATURE

Figure 1:
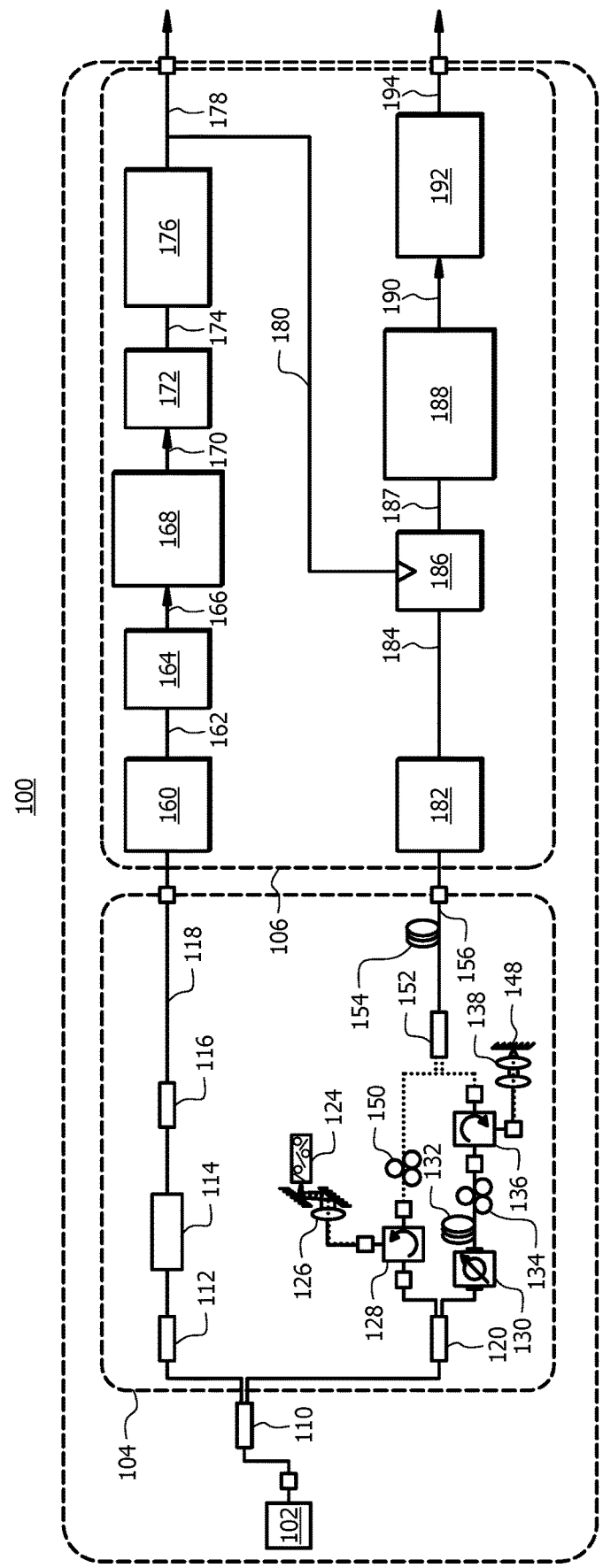
FIG. 1 shows an illustrative block diagram of a SS-OCT calibration system in accordance with various embodiments.

Certain terms are used throughout the following description and claims to refer to particular system components. As one skilled in the art will appreciate, entities and/or individuals may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices and connections. The recitation "based on" is intended to mean "based at least in part on." Therefore, if X is based on Y, X may be based on Y and any number of other factors.

DETAILED DESCRIPTION

The following discussion is directed to various embodiments of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Conventional SS-OCT interferometers and SS-OCT optical processing systems typically calibrate and/or process the interferometric optical signal by one of two processes. One conventional process samples and stores both the calibrating signal and the interferometric signal, processes the calibrating signal in software, and then derives an image from the interferometric signal based on the processed calibrating signal. This approach is processing intensive and time consuming. Partly this approach is time consuming because it samples and stores many values of the interferometric signal that are discarded in processing because they do not align with linear k values in the calibrating signal. Said in other words, a few particular calibration signal values are selected from a large number of calibration signal values and these selected particular calibration signal values are used to calibrate a few interferometric signal values that correspond to the few selected calibration signal values and the remaining interferometric signal values are discarded. The other conventional process samples the calibrating signal, tracks the calibrating signal to detect when its value crosses a zero threshold (determine zero-crossings), and samples the interferometric signal on the event that a calibration signal zero-crossing occurs. This process suffers from slow processing in that the zero crossing events are relatively rare, which inherently delays the capturing of the desirable number of interferometric signal data points for processing to construct the image. Moreover, in some examples of the conventional process, the lack of sufficient points sacrifices other performance metrics that may be important when design SS-ODC systems.

The present disclosure teaches a different system for determining suitable times to sample and process the interferometric signal that does not suffer from the drawbacks of the two conventional processes. The optical calibrating signal is converted to an electrical calibrating signal. The electrical calibrating signal is converted from an analog calibrating signal to a sequence of digital calibrating signal values (e.g., is converted and sampled). The sequence of digital calibrating signal values are demodulated to extract the wave number associated with each digital calibrating signal value. The wave number is tracked as it ramps monotonically. When the wave number crosses one of a plurality of pre-defined wave number values (e.g., a pre-defined level crossing), a calibrating clock pulse is generated. The optical interferometric signal is converted to an electrical interferometric signal. The calibrating clock pulse is used to time and/or trigger a digital-to-analog conversion sampling of the electrical interferometric signal at a time such that the pre-defined wave number associated with the clock pulse corresponds with the wave number associated with the sample of the electrical interferometric signal. The electrical interferometric signal is processed based on the known wave number associated with the electrical interferometric signal sample, thereby simplifying and increasing the accuracy of the image extraction. This novel system and process overcomes the limitations described above with reference to the two customary approaches to calibrating SS-OCT. The SS-OCT system and method of the present disclosure can capture interferometric signal as fast as the light source can scan. The SS-OCT system and method of the present disclosure can save the effort of more complicated processing involved in two conventional systems. Additionally, the precise matching of the wave number to the selected interferometric signal sample promotes greater resolution and precision than may be achieved in conventional systems.

The problems noted above are solved in large part by systems and methods for performing spectral calibration demodulation (via techniques including but not limited to square law envelope detection, Kalman filtering, and interpolated discrete Fourier transformation for demodulation purposes) in SS-OCT interferometers and novel non-uniform/asynchronous samplers (including but not limited to continuous time ternary encoder, CTTE, sampler). In some embodiments, a calibration clock is created utilizing an auxiliary calibrating signal (including but not limited to a Mach-Zehnder interferometer, MZI signal). The calibrating clock signal is used to provide a high resolution image by improving the axial resolution by several micrometers. In examples, applying the teachings herein may produce tomographic images at higher rates as well as capturing cubic meter tomographic images. In some examples, the teachings of the disclosure may enable the swift shift of SS-OCT systems into real-time MHz data acquisition regimes.

An illustrative embodiment is an interferometer system for performing spectral calibration in SS-OCT systems comprised primarily of two blocks: an electronic processing device and an enclosure with optical and/or electrical fixtures. The optical components may be implemented on-chip or discrete components may be used. A printed circuit board (PCB) may reside within the enclosure. The PCB may include one or more signal processing devices that may include, but are not limited to: microcontrollers (MCUs), microprocessor unites (MPUs), digital signal processors (DSPs), field programmable gate-arrays (FPGAs), photodetection devices (e.g., InGaAs photodiodes), data acquisition devices (e.g., digital-to-analog converters (DACs), analog-to-digital converters (ADCs), and non-uniform/asynchronous samplers, (level crossing samplers including but not limited to a Continuous Time Ternary Encoding Sampler), amplification devices, etc. These devices can be systems on chip (SoC) or can be off the shelf components. The enclosure may be a custom built enclosure for housing and electronic shielding of the PCB and/or optical components. The enclosure may include one or more components that may include, but are not limited to: metallic radio frequency shielding sheets, electronic fixtures, switches, selection devices, graphical user interface devices (e.g., tactile displays and selection menus), plastic and optical fixtures, etc. In an embodiment, the enclosure may be metal.

FIG. 1 shows an illustrative block diagram of a SS-OCT calibration system 100 in accordance with various embodiments. The calibration system 100 may include a swept source laser 102, an optical block 104, and an electronics block 106. The optical block 104 may be made with either integrated or discrete optical components. The swept source laser 102 may be any type of swept source laser at any wavelength regime (Including but not limited to center wavelengths of 850 nm, 1050 nm, 1220 nm, 1310 nm, 1550 nm, and sweep ranges of 60 nm, 90 nm, 80 nm, 110 nm, 110 nm, respectively with different A-scan sweep rates). The light is split by a first splitter 110 into a less powerful optical path utilizing, in some embodiments, 5% of the emitted light from the laser 102 (i.e., a reference path) and a more powerful path utilizing, in some embodiments, 95% of the emitted light from the laser 102 (i.e., a sample path). The sample path light is projected through the object to be imaged (e.g., tissue) and received by the optical block 104. The optical block 104 also receives the reference path light as well. The optical block 104 performs optical operations to produce two different optical outputs: an optical calibrating signal 118 which will be used as a reference signal and an optical interferometric signal 156 corresponding with the object under test (i.e., the signal received after passing through the tissue under test).

In an embodiment, the reference path comprises a second splitter 112, a Mach-Zehnder interferometer (MZI) 114, and a third splitter 116. In some contexts the optical calibrating signal 118 may be referred to as a MZI optical signal. In an embodiment, the sample path of the optical block comprises a fourth splitter 120, a first circulator 128 an optical transmitter/receiver 126, an attenuator 130, a first optical delay line 132, a first polarization controller 134, a second circulator 136, a lens combination 138, a reference mirror 148, a second polarization controller 150, a fifth splitter 152, and a second optical delay line 154.

The electronics portion 106 is configured to perform a demodulation process and to perform ultra-fast data acquisition of swept source optical coherence tomography in real time, without the need for external computational devices. In an embodiment, the electronics portion 106 is configured to receive both the calibrating signal and the interferometric input signal and process those signals to generate either a calibrating clock or the tomographic image itself depending on the application the device is intended to be used in.

In an embodiment, the electronics portion 106 comprises a photodetector 160, a second photodetector 182, an analog-to-digital converter (ADC) 164, a second ADC 186, a processing unit 168, a digital-to-analog converter (DAC) 172, a level crossing sampler 176, an asynchronous to synchronous converter 188, and an auxiliary signal processor 192. In different embodiments, the electronics portion 106 may comprise different components. For example, in an embodiment that generates a calibrating clock only, the second photodetector 186, the second ADC 186, the asynchronous to synchronous converter 188, and the auxiliary signal processor 192 may be omitted. In an embodiment in which calibration signal level crossing is performed in the digital domain, the electronics portion 106 may omit the level crossing sampler component 176 (e.g., level sampling may be implemented as a software component executed by the processing unit 168 rather than by a separate circuit). In an embodiment, the electronics portion 106 may be constructed from separate components. Alternatively, in an embodiment, the electronics portion 106 may be integrated in an integrated circuit or as a system on a chip (SoC).

In an embodiment, the first photodetector 160 is coupled to the first analog-to-digital converter (ADC) 164. The first ADC 164 is coupled to the processing unit 168. The processing unit 168 is coupled to the digital-to-analog converter (DAC) 172. The DAC 172 is coupled to the level crossing sampler 176. The second photodetector 182 is coupled to the second ADC 186. The second ADC 186 is coupled to the output of the level crossing sampler 176 (e.g., coupled to receive the calibrating clock signal 178 output by the level crossing sampler 176) and coupled to the asynchronous to synchronous converter 188. The asynchronous to synchronous converter 188 is coupled to the auxiliary signal processor 192.

The photodetectors 160, 182 may be wideband photodetectors 160, 182 that convert the optical signals to electrical signals. In an embodiment, the photodetectors 160, 182 may be InGaAs photodiodes. In another embodiment, the photodetectors 160, 182 may comprise a different kind of photodiode based on a different semiconductor material. The first photodetector 160 receives the optical calibrating signal 118 and converts it to an electrical calibrating signal 162. The first ADC 164 receives the electrical calibrating signal 162 and converts it to a sequence of digital calibrating signal values 166. The processing unit 168 processes the sequence of digital calibrating signal values 166 to extract a wave number of each of the sequence of digital calibrating signal values and outputs a sequence of digital wave number values 170 to the DAC 172. The DAC 172 converts the sequence of digital wave number values 170 to an analog wave number signal 174 that may be represented as k(t). The analog wave number signal 174 is provided to the level crossing sampler 176. A second photodetector 182 receives the optical interferometric signal 156 and converts it to an electrical interferometric signal 184. The level crossing sampler 176 tracks the analog wave number signal 174 and outputs a calibrating clock signal 178. The calibrating clock signal 178 comprises a series of pulses, where each pulse is generated by the level crossing sampler 176 when a predefined wave number k threshold is passed. The calibrating clock signal 178 can be produced with a falling edge (e.g., an inactive state of the clock signal is a low value and the level crossing event is indicated by a falling pulse that rises back to the non-eventful high value) or with a rising edge (e.g., an inactive state of the clock signal is a low value and the level crossing event is indicated by a rising pulse that falls back to the non-eventful low value).

In an embodiment, the level crossing sampler 176 outputs this calibrating clock signal 178 to be used by an external system. In such an embodiment, the interferometric signal handling path comprising the second photodetector 182, the second ADC 186, the asynchronous to synchronous converter 188, and the auxiliary signal processor 192 may not be present in the electronics portion 106. In an embodiment, the level crossing sampler 176 outputs a calibrating clock signal 180 to the second ADC 186 which triggers the second ADC 186 to sample the electronic interferometric signal 184 at a point when the electrical interferometric signal 184 matches to the wave number level crossing. It is noted that optical delay line 154 can be configured to delay the optical interferometric signal 156 very precisely such that the processing of the optical calibrating signal 118 can be performed and the wave number level crossing event detected and responded to just as the associated electrical interferometric signal 184 is arriving at the second ADC 186 to be captured in a sample. The second ADC 186 outputs a sequence of digital electronic interferometric signal values 187 to the asynchronous synchronous converter 188. In some contexts, the sequence of digital electronic interferometric signal values may be referred to as a sequence of calibrated digital electronic interferometric signal values. The asynchronous to synchronous converter 188 stores and accumulates the sequence of digital electronic interferometric signal values 187 associated with the same point on the sample 124 with asynchronous timing (e.g., the samples are taken at irregular time intervals, because the wave number crossings induced by the sweep of the laser 102 exhibits irregular time intervals). The stored digital electronic interferometric signal values 187 associated with the same point on the sample (same laser frequency sweep cycle) can be read out of the asynchronous to synchronous converter 188 by the auxiliary signal processor 192 synchronously.

Figure 2:
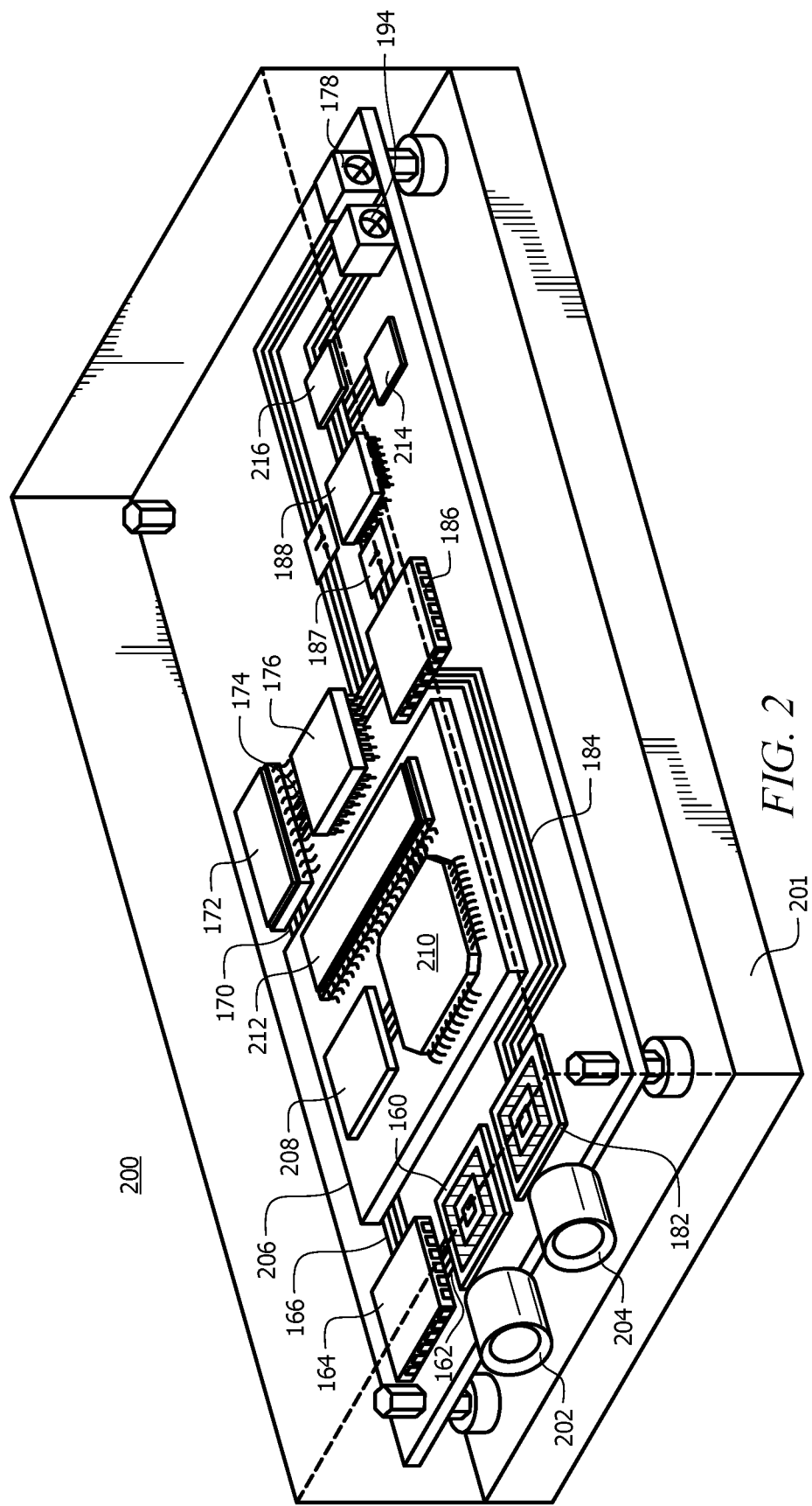
FIG. 2 shows an illustrative three dimensional (3D) schematic diagram of an enclosure that protects a PCB for signal processing in a SS-OCT system in accordance with various embodiments.

FIG. 2 shows an illustrative three dimensional (3D) schematic diagram of electronic components of an enclosure 200 that protects a PCB (e.g., the electronic portion 106) that electrically connects the remaining electronics in the enclosure 200 for signal processing in SS-OCT system 100 in accordance with various embodiments. The enclosure 200 may be metallic to protect the electronic portion 106 within. The electronic portion 104 in FIG. 2 comprises a digital signal processor module 206 that corresponds to the processing unit 168 of FIG. 1. In an embodiment, the digital signal processor module 206 comprises a system parameters observer component 208, a processing unit 210, and a memory 212. The processing unit 210 may comprise a microcontroller (MCU), a microprocessor unit (MPU), a digital signal processor (DSP), a field programmable gate array (FPGA), an application specific integrated circuit (ASIC), or other semiconductor logic processor device.

The level crossing sampler 176 produces a pulse every time the wave number signal 174 is increased or decreased by identical predefined values. In some contexts, the wave number signal 174 may be referred to as a calibration profile. If the operation to be performed by the electronic portion 106 is to generate a calibrating clock, then the ADC 164 may be configured to receive the electrical calibration signal 162 (e.g., the MZI signal produced by the reference path of the optical portion 104 converted to electrical domain) from the first photodetector 160 while the signal representative of the interferometric input is discarded.

The DSP module 206, and more particularly, the processing unit 210, may be configured to demodulate the sequence of digital electronic calibrating electrical signal values 166 in real time. In examples, the teachings of the present disclosure may enable the real-time calibration of the SS-OCT devices in MHz regimes. In some examples, the demodulation may utilize any real time demodulation algorithm. For example, the calibrating electrical signal may be filtered prior to demodulation. In some embodiments, the DSP module 206 may utilize a simple square law envelope detector filter to generate a filtered calibrating electrical signal to enable the generation, by the DSP module 206, of a calibration profile (e.g., the sequence of digital wave number values), although other filter techniques may be employed. The DSP module 206 may utilize a Kalman filter to demodulate the sequence of digital calibrating electrical signal values and generate the calibration profile, although other techniques may be employed. For example, a Fourier transform may be employed on the sequence of digital electronic calibration signal values with which the wavenumber sweeping non-linearity is cancelled, in some embodiments, utilizing an interpolated discrete Fourier transform (IpDFT). The DSP module 206 then may produce a calibration profile that is processed by the level crossing sampler 176. It is understood that in different embodiments, other level crossing/asynchronous sampling techniques may be employed. It should be noted that the electrical calibration signal (including but not limited to a MZI-type calibration signal) can be modeled as an amplitude modulated chirp in which the calibration profile is modulated. Its value can be modeled as, $$I_{MZI}(t) = Cs(t)\cos(k(t)),\qquad \text{EQ 1}$$

$$I_{MZI}(n) = Cs(n)\cos(k(n)),\qquad \text{EQ 1'}$$

where C is a constant, s(t) denotes power spectral dependence of the light source (e.g., swept source laser) sweep, and k(t) denotes the wave number (note that EQ1 represents the electrical calibration signal in the continuous domain while EQ1' represents the corresponding digital domain equation relating to the sequence of digital electrical calibration signal values that are processed by the DSP module 206 in the digital domain). Techniques mentioned above (included but not limited to simple square law envelope detection, Kalman filtering, and interpolated discrete Fourier transformation) are intended to extract k[n] (the wave number associated with sample number n) from the MZI signal in an efficient manner. The extraction process is referred to as demodulation in some contexts herein.

The DAC 170 converts the sequence of digital wave number values 170 (k(n) and converts these values 170 to the wave number signal 174 (e.g., analog signal k(t)) and provides the wave number signal 174 to the level crossing sampler 176. As discussed above, the level crossing sampler 176 may receive the wave number signal 174 (e.g., calibration profile k(t)) and produce an asynchronous clock that can be used to sample the interferometric electrical signal 184 produced by photodetector 182 by the second ADC 186. The interferometric signal, $I_D(t)$, is conventionally formulated as below, $$I_D(t) = \frac{\rho}{4}[s(t)[R_R + R_{S1} + R_{S2} + R_{S3} + \ldots]] + \qquad \text{EQ2}$$
$$\frac{\rho}{2}\left[s(t)\sum_{n=1}^{N}\sqrt{R_R R_{Sn}}\,(\cos[2k(t)(z_R - z_{Sn})])\right] +$$
$$\frac{\rho}{4}\left[s(t)\sum_{n\neq m=1}^{N}\sqrt{R_{Sm} R_{Sn}}\,(\cos[2k(t)(z_{Sm} - z_{Sn})])\right]$$

where $\tau$, $s(t)$, $R_R$, $R_{Sn}$, $z_R$, and $z_{Sn}$ are values that depend on the optical configuration. The n-number of values $R_{Sn}$ is the power reflectivity of different particles within the object to be imaged and are the values to be found to build a tomographic image. In SS-OCT systems (including the present disclosure) an Inverse Fast Fourier Transformation is applied on $I_D$ to capture the parameters $R_{Sn}$. Knowing that k(t) is not sweeping linearly in time, it can be observed that if $I_D(t)$ is sampled with uniform clocks, the parameters $R_{Sn}$ cannot be accurately captured by applying a conventional Inverse Fast Fourier Transformation; hence the need to sample $I_D(t)$ non-uniformly in time. The non-uniform calibrating time instances at which $I_D(t)$ needs to be sampled are denoted as $t_c$ and can be related to k(t) as below, $$t_c = k^{-1}(k_c)$$

Said in other words, the demodulation performed by the DSP module 206 described above transforms the term k(t) to a constant: when the sample of the electric interferometric signal 184 is taken, the wave number value of k(t) is a known, predefined wave number value $k_c$. Using these time instances we can perform a non-uniform sampling on the signal $I_D(t)$—the time instances signaled by the event of the pulse of the calibration signal 180—the calibrated interferometric signal can be expressed as, $$I_D(t_c) = \frac{\rho}{4}[s(t_c)[R_R + R_{S1} + R_{S2} + R_{S3} + \ldots]] + \qquad \text{EQ3}$$
$$\frac{\rho}{2}\left[s(t_c)\sum_{n=1}^{N}\sqrt{R_R R_{Sn}}\,(\cos[2k_c(z_R - z_{Sn})])\right] +$$
$$\frac{\rho}{4}\left[s(t_c)\sum_{n\neq m=1}^{N}\sqrt{R_{Sm} R_{Sn}}\,(\cos[2k_c(z_{Sm} - z_{Sn})])\right]$$

Inspection of EQ3 reveals that EQ3 is more readily solved for the parameters $R_{Sn}$ than EQ2. Once the newly asynchronously sampled interferometric signal ($I_{D,calibrated}[n]$) is acquired, a conventional Inverse Fast Fourier Transformation can be applied and the parameter $\sqrt{R_{Sn}}$ can be captured. As the calibrated signal, $I_{D,calibrated}[n]$, is sampled via an asynchronous clock an asynchronous to synchronous converter block needs to be used so that the following blocks can fetch this data via synchronous clocks. Furthermore, auxiliary signal processing operations are performed to address other non-idealities including but not limited to background subtraction and dispersion correction. These auxiliary signal processing operations are performed by means of another DSP block. Like the calibration clock signal 178, the electrical interferometric signal 184 that is sampled by the second ADC 186 responsive to the asynchronous clock is received by an output selector 187 which selects which output to generate based on the type of operation. For example, the output selector 187 will select the calibration clock signal 178 if the operation is an operation only produce a calibrating clock. Thus, the calibrating clock will be received by one or more of the analog outputs 194 to be output from the enclosure 200. The output selector 187 will select the interferometric signal 184 (tomographic signal) if the operation is a full image extraction operation. Thus, the electrical interferometric signal 184 (tomographic signal) will be received by one or more of the analog outputs 194 to be output from the enclosure 200 to, in some embodiments, a graphical user interface or to a monitor.

Figure 3:
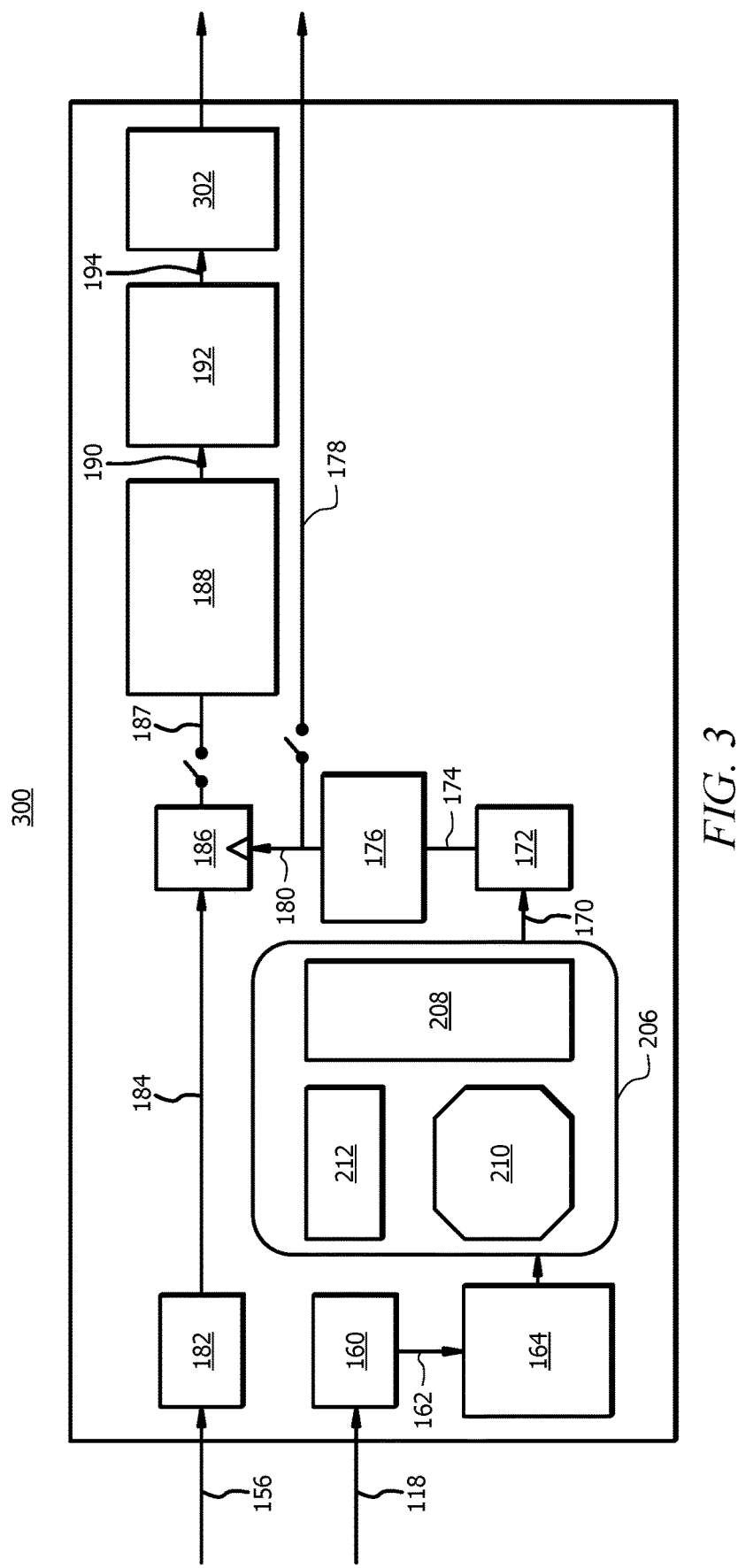
FIG. 3 shows an illustrative signal flow block diagram showing system block interactions in a SS-OCT system in accordance with various embodiments.

FIG. 3 shows an illustrative signal flow block diagram showing system block interactions in the electronic portion 106 in accordance with various embodiments. The signal flow block diagram shown in FIG. 3 provides the signal flow as discussed above with respect to the electronic portion 104 with reference to FIG. 1 and with respect to the enclosure 200 with reference to FIG. 2. In system 300, a graphics controller 302 may be coupled to the asynchronous to synchronous converter 188 and may be configured to receive the interferometric signal from the asynchronous to synchronous converter 188 and process the signal for display on a graphical user interface. Thus, a calibrating clock and an output image of the tomographic signal may be generated by the electronic portion 106 as discussed above.

Figure 4:
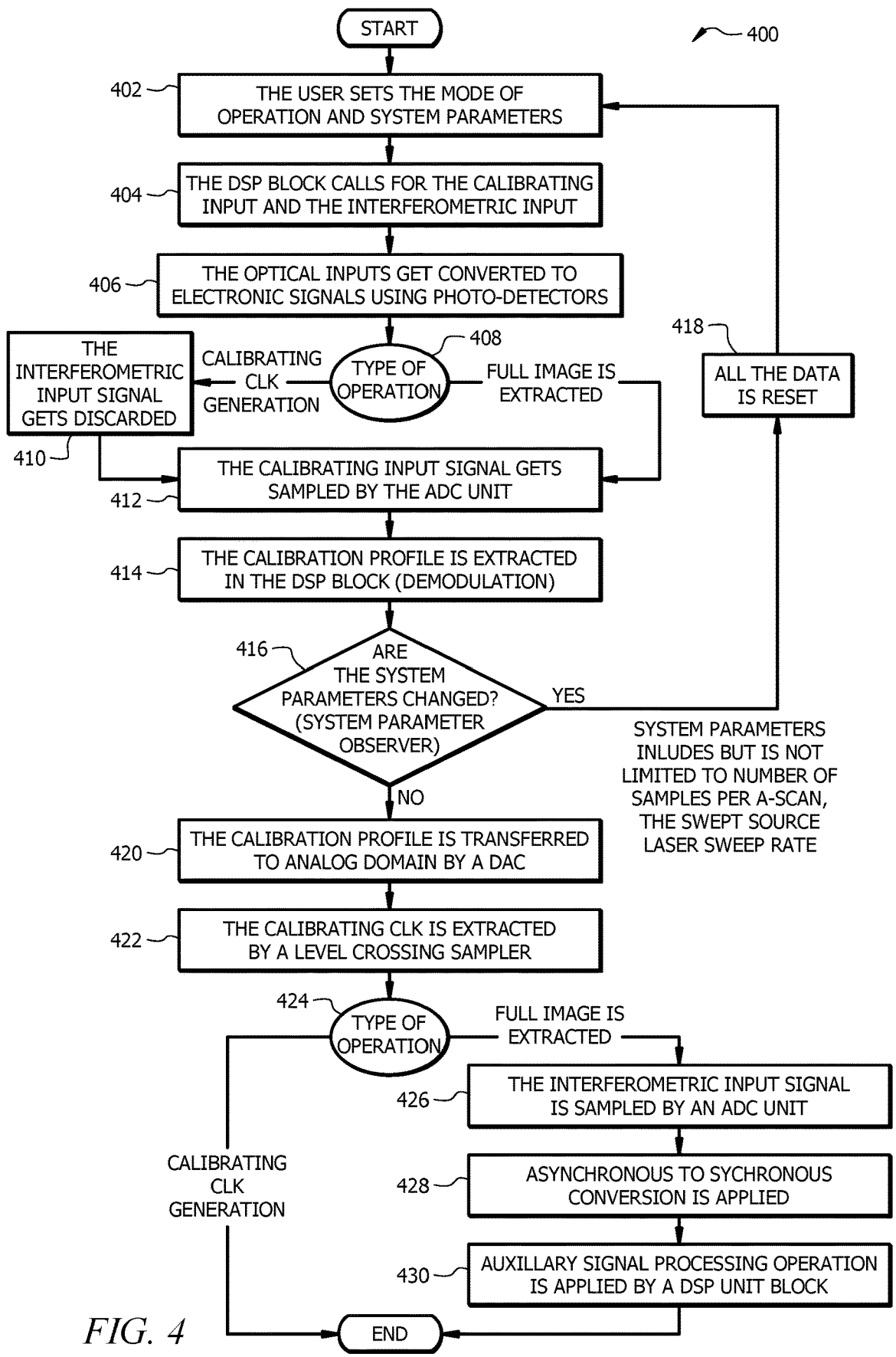
FIG. 4 shows an illustrative flow block diagram of a method for performing spectral calibration of SS-OCT interferograms in accordance with various embodiments.

FIG. 4 shows an illustrative flow block diagram of a method 400 for performing spectral calibration in SS-OCT interferograms in accordance with various embodiments. Though depicted sequentially as a matter of convenience, at least some of the actions shown can be performed in a different order and/or performed in parallel. Additionally, some embodiments may perform only some of the actions shown. In some embodiments, at least some of the operations of the method 400, as well as other operations described herein, can be performed by the circuits described above, for example by the electronic portion 106, the circuitry contained within the enclosure 200, system 300, and/or implemented in logic and/or by a processing unit executing instructions stored in a non-transitory computer readable storage medium.

The method 400 begins in block 402 with setting a mode of operation and system parameters. For example, a user may select whether the system is operating to generate a calibrating clock or a full image extraction. The user may as well indicate the system parameters they choose to operate at. The parameters include but are not limited to the number of points necessary to be sampled per laser sweep and/or the speed at which the laser sweeps. In block 404, the method 400 continues with calling for a calibrating signal and an interferometric signal from the optical portion 104. Thus, for example, a DSP may call the optical portion 104 to transmit the optical calibrating signal and the optical interferometric signal.

The method 400 continues in block 406 with converting the optical calibrating signal and the optical interferometric signal into the electrical domain. For example, one or more photodetectors may convert the optical signals to currents representative of the optical signals. In block 408, the method 400 continues based on the mode of operation (i.e., whether the mode of operation set by the user is a generating calibrating clock mode or a full image extraction mode). In block 410, the method 400 continues with, based on the mode of operation being a generate calibrating clock mode, discarding the interferometric signal. The method 400 continues in block 412, which operates in both modes of operation, with sampling the calibrating electrical signal. In block 414, the method 400 continues with extracting the calibration profile, k(t), from the sampled calibrating electrical signal.

The method 400 continues in block 414 with determining whether the parameters/conditions the system works in has changed within the calibration profile. If, in block 414, a determination that the condition/parameters the system works in (e.g., number of points to be sampled in each A-scan) has changed within the calibration profile, the method 400 continues in block 418 with resetting the calibration process. The method 400 then continues in block 402 with setting the mode of operation and system parameters. However, if, in block 414, a determination that the system parameters/conditions has not changed within the calibration profile, the method 400 continues in block 420 with extracting the calibration profile from the sampled calibrating electrical signal. In block 422, the method 400 continues with extracting the calibrating clock from the calibration profile.

The method 400 continues in block 424 based on the mode of operation (i.e., whether the mode of operation set by the user is a generating calibrating clock mode or a full image extraction mode). In block 426, the method 400 continues with, based on the mode of operation being a full image extraction operation, sampling the interferometric signal. The method 400 continues in block 428 by performing an asynchronous to synchronous conversion. The method 400 continues in block 428 with performing auxiliary signal processing on the sampled interferometric signal to generate the tomographic image. The method 400 ends in block 432 with a calibrating clock generated and/or a full image extracted.

Figure 5A:
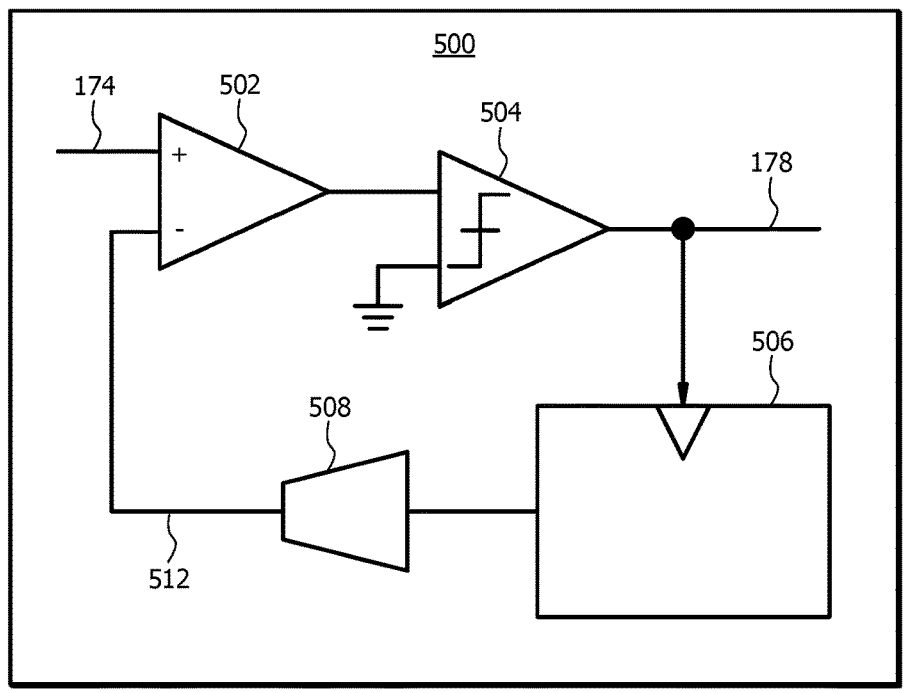
FIG. 5A shows an illustration of a level crossing sampler in accordance with various embodiments.
Figure 5B:
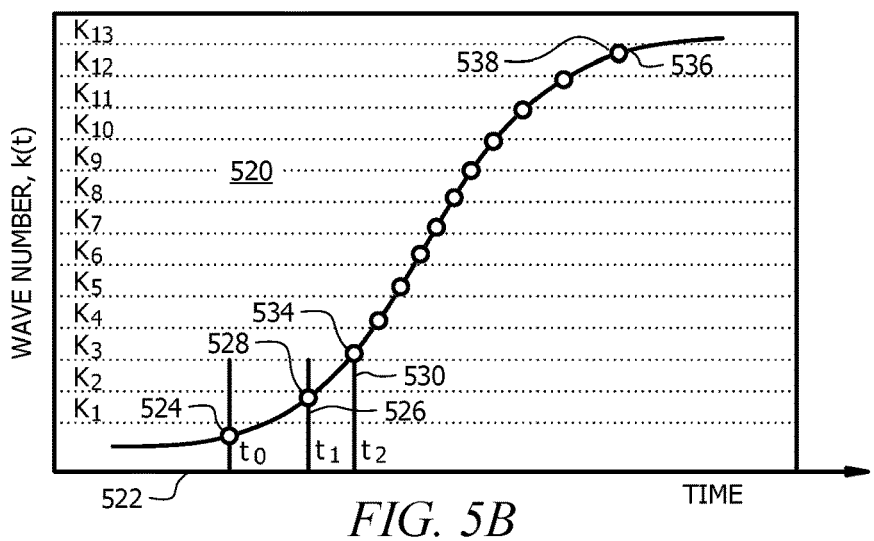
FIG. 5B shows a graph of an exemplary wave number versus time curve in accordance with various embodiments.
Figure 5C:
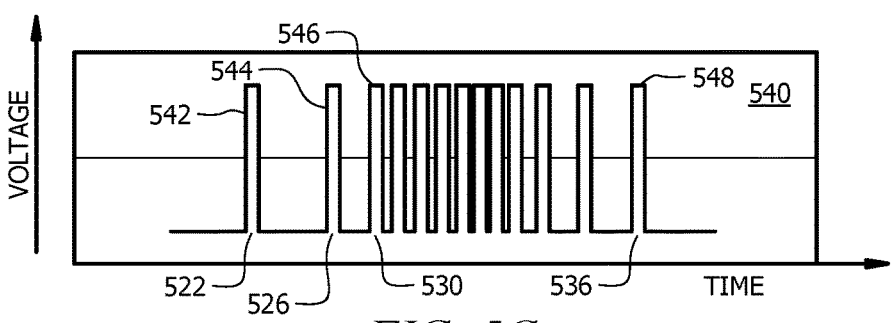
FIG. 5C shows a graph of an exemplary calibration clock signal in accordance with various embodiments.

FIG. 5A, FIG. 5B, and FIG. 5C illustrate an embodiment of a level crossing sampler 500 that processes the analog wave number signal 174 (k(t)) to determine when each of a plurality of predefined levels or values of wave number are passed and to generate an asynchronous calibration clock 178. The level crossing sampler 500 comprises an operational amplifier 502, a comparator 504, an asynchronous accumulator 506, and second DAC 508. The second DAC 508 outputs a reference signal 512 that is provided to a negative input of the operational amplifier 502. The output of the second DAC 508 provides a reference that corresponds to one of the predefined levels and/or predefined wave number values. As the swept source laser 102 is swept in frequency and the wave number extracted by the electronics portion 106, the analog wave number signal 174 increases until it equals and then exceeds the reference signal 512, at which point the operational amplifier output flips from strongly negative to strongly positive. This positive output of the operational amplifier 502 is received by the comparator 504 and causes it to generate a logic high signal. This logic high signal is the calibration clock signal 178 and is fed into a clock input of the asynchronous accumulator 506. The clock transition causes the asynchronous accumulator 506 to increment its digital output to the second DAC 508, causing the second DAC 508 to increment the output of the reference signal 512 to the next higher predefined reference value. The analog wave number signal 174 is now lower in value than the reference signal 512, and the output of the operational amplifier 502 swings from strongly positive to strongly negative. This drives the output of the comparator 504 to logic low. It is understood that in an alternative embodiment, the polarity of the operational amplifier 502 may be reversed or a logic inverter may be coupled to receive the output of the comparator 504, such that the calibrating clock polarity is reversed. When the swept source laser 102 has completed its scan, the level crossing sampler 500 may be reset, such that the asynchronous accumulator 506 is reset to an initial digital counting value, for example to a 0 value.

FIG. 5B illustrates an exemplary wave number versus time plot 520 of a frequency sweep of the swept source laser 102. This It is understood that the shape of the wave number versus time profile may vary from sweep to sweep of the swept source laser 102 through a range of frequencies or as different swept source lasers are used. As indicated in FIG. 5B, in examples the wave number is not a linear function of time. The plot 520 comprises 13 points where the swept wave number crosses predefined wave number values $K_1$, $K_2$, $K_3$, . . . , $K_{13}$. A first point 524 of the plot 520 shows that the swept source laser 102 sweeps the light through the wave number $K_1$ at a first time 522 ($T_0$), a second point 528 shows the source 102 sweeps through the wave number $K_2$ at a second time 526 ($T_1$), a third point 534 shows the source 102 sweeps through the wave number $K_3$ at a third time 530 ($T_2$), and a thirteenth point 538 shows the source 102 sweeps through the wave number $K_{13}$ at a fourth time 536. It is understood that the swept source laser 102 may sweep through any range of wave numbers and that the electronic portion 104 may predefine any number of wave numbers to trigger a calibration clock pulse. The level crossing sampler 500 may track the wave number values and generate a pulse at times corresponding to the swept source laser 102 achieving the predefined wave number values. The predefined wave numbers may be equally spaced from each other, for example the difference between each two adjacent wave numbers may be equal to the difference between any other two adjacent wave numbers.

FIG. 5C illustrates calibration clock pulses 540 corresponding to the level crossings (e.g., the passing of the wave number of the swept source laser 102 above a predefined wave number) illustrated in FIG. 5B. A first pulse 542 is generated at time 522 as the wave number of the swept source laser 102 passes through wave number $K_1$. A second pulse 544 is generated at time 526 as the wave number of the swept source laser 102 passes through the wave number $K_2$, a third pulse 544 is generated at time 530 as the wave number of the swept source laser 102 passes through the wave number $K_3$, and a fourth pulse 548 is generated at time 536 as the wave number of the swept source laser 102 passes through the wave number $K_{13}$. It is noted that the time between the wave number of the swept source laser 102 crossing the predefined wave numbers $K_1, K_2, K_3, \ldots, K_{13}$ are not equally spaced. Some of the time increments between crossings of adjacent predefined wave numbers K are different from the time increments between crossings of different adjacent predefined wave numbers K.

Figure 6A:
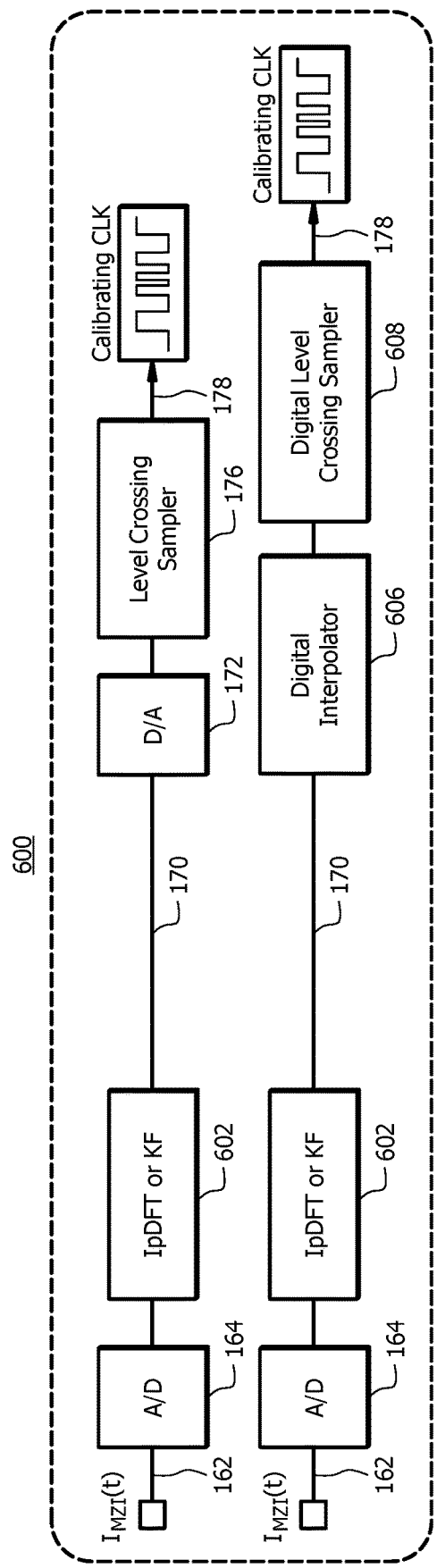
FIG. 6A shows an illustrative signal processing flow in accordance with various embodiments.

FIG. 6A illustrates an approach to extracting the wave number from the electrical calibration signal 162 and generating the calibration clock signal 178, 180 based on the wave number, based on using a first demodulation approach that relies upon either Kalman filtering or interpolated discrete Fourier transform processing the sequence of digital wave number signal values 166. The demodulation operation is illustrated in FIG. 6A as a demodulation component 602 that may be implemented in software, firmware, or electronic logic. The level crossing sampling and generation of the calibration clock signal 178, 180 can be done in either the analog domain (the upper portion of FIG. 6A) or in the digital domain (the lower portion of FIG. 6A). In the digital domain, the sequence of digital wave number values is processed by a digital interpolator 606, and the output of the digital interpolator 606 is processed by a digital level crossing sampler 608 to generate the calibration clock signal 178, 180. In an embodiment, an analog filter may be placed at the output of the digital level crossing sampler 608 to smooth and/or to debounce the output of the digital level crossing sampler 608.

Figure 6B:
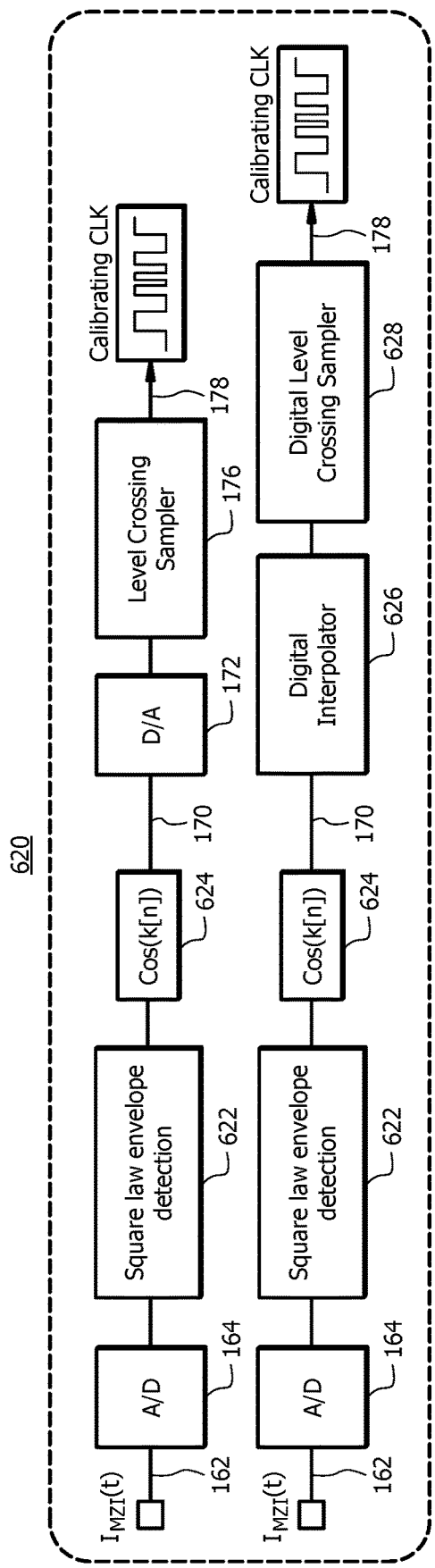
FIG. 6B shows another illustrative signal processing flow in accordance with various embodiments.

FIG. 6B illustrates another approach to extracting the wave number from the electrical calibration signal 162 and generating the calibration clock signal 178, 180 based on the wave number, based on using a second demodulation approach that relies on square law envelope detection followed by a cosine function processing the sequence of digital wave number signal values 166. The demodulation operation is illustrated in FIG. 6B as a demodulation component 622 that yields a cosine of the calibration profile 624.The level crossing sampling and generation of the calibration clock signal 178, 180 can be done in either the analog domain (the upper portion of FIG. 6B) or in the digital domain (the lower portion of FIG. 6B) by driving the level crossing sampling blocks by the cosine of the calibration profile. In the digital domain, the sequence of digital wave number values is processed by a digital interpolator 626, and the output of the digital interpolator 626 is processed by a digital level crossing sampler 628 to generate the calibration clock signal 178, 180. In an embodiment, an analog filter may be placed at the output of the digital level crossing sampler 628 to smooth and/or to debounce the output of the digital level crossing sampler 628.

Figure 7:
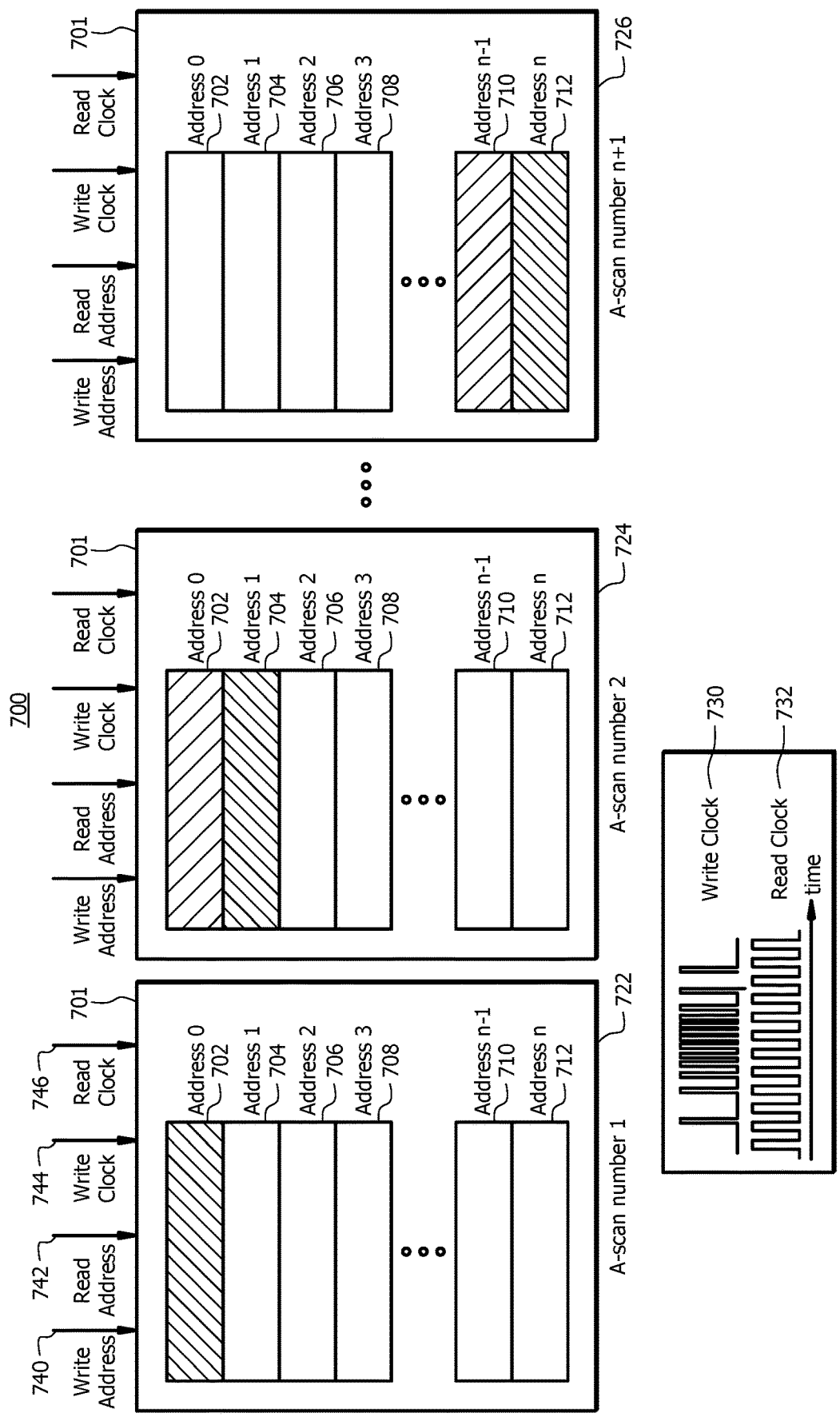
FIG. 7 shows an illustration of an asynchronous to synchronous converter in accordance with various embodiments.

Turning now to FIG. 7, an exemplary operation of an asynchronous to synchronous converter 188 is illustrated.

Because the electrical interferometric signal 184 is sampled on clock events in the calibration clock signal 180, and because these clock events are asynchronously timed, the sequence of digital interferometric signal values are generated asynchronously. But yet downstream consumers of the interferometric signal may desire to read the interferometric signal synchronously (e.g., reading on regular period intervals). The asynchronous to synchronous converter 188 stores a sequence of digital interferometric values associated with the same sweep of frequency of the swept source laser 102 in a first block of memory. When the sweep of the swept source laser 102 is complete and the next sweep of the swept source laser 102 starts, the asynchronous to synchronous converter 188 stores the next sequence of digital interferometric values associated with the next sweep of frequency of the swept source laser 102 in a second block of memory. Meanwhile, a consumer (e.g., the auxiliary signal processor 192 of FIG. 1) of the digital interferometric values can read the values associated with the first sweep of the swept source laser 102 synchronously from the asynchronous to synchronous converter 188.

In an embodiment, the asynchronous to synchronous converter 188 comprises a memory 701 that is accessed by controls write address 740, read address 742, write clock 744, and read clock 746. The memory 701 comprises a plurality of memory blocks including a first memory block 702 at address 0, a second memory block 702 at address 1, a third memory block 703 at address 2, a fourth memory block 704 at address 3, a fifth memory block 710 at address n−1, and a sixth memory block 712 at address n. During a first sweep of the swept source laser 102 (first A-scan number 722) a sequence of calibrated digital interferometric signal values are written into the first memory block 702. During a second sweep of the swept source laser 102 (second A-scan number 724), a sequence of calibrated digital interferometric signal values are written into the second memory block 704 and the sequence of digital interferometric signal values stored in the first memory block 702 may be read out by a consumer. During a third sweep of the swept source laser 102 (third A-scan number 726), a sequence of calibrated digital interferometric signal values are written into the third memory block 706 and the sequence of digital interferometric signal values stored in the second memory block 704 may be read out by a consumer. This sequence of asynchronous writes of a sequence of digital interferometric signal values into a memory block during a current frequency sweep of the swept source laser 102 while with concurrent synchronous reads of a sequence of digital interferometric signal values from a previously written memory block continues indefinitely until the interferometric image capture process is completed. When the last memory block (e.g., sixth memory block 712) is written, the asynchronous to synchronous converter 188 can begin overwriting the first memory block 702, using the memory 701 in a circular fashion.

A write clock 730 may be derived from the calibration clock signal 178, 180 and used to control writing to the memory 701. A synchronous read clock 732 can be used by a consumer to read the digital interferometric signal values out of the memory blocks 702, 704, 706, 708, 710, 712. In an embodiment, there may be a linkage between the asynchronous clock 730 and the synchronous clock 732 that constitutes a framing clock linkage. For example, a digital divider may divide the asynchronous calibration clock signal 178, 180 by the number of different predefined wave numbers (e.g., divide by 13 in the example of FIG. 5A, FIG. 5B, and FIG. 5C) and use a pulse generated when the divided clock rolls over as a framing signal to align the start of reading the next block of memory.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

The invention claimed is:

1. A circuit for generating a swept source optical coherence tomography (SS-OCT) imaging calibration clock, comprising:
   a first photodetector configured to convert an SS-OCT optical calibration signal to an SS-OCT electrical calibration signal;
   a first analog-to-digital converter (ADC) coupled to the first photodetector and configured to convert the SS-OCT electrical calibration signal to a sequence of SS-OCT calibration signal digital values;
   a processing unit coupled to the first ADC that, when initiated, is configured to demodulate the sequence of SS-OCT calibration signal digital values to obtain a sequence of SS-OCT wave number digital values, where each SS-OCT wave number digital value corresponds to one of the SS-OCT calibration signal digital values;
   a level crossing sampler that is configured to track a wave number associated with the SS-OCT optical calibration signal and to generate an SS-OCT calibration clock pulse, whereby an SS-OCT interferometric optical signal is sampled based on the SS-OCT calibration pulse.

2. The circuit of claim 1, where the first photodetector is a InGaAs photodiode.

3. The circuit of claim 1, where the processing unit is configured to demodulate the sequence of SS-OCT calibration signal digital values using a Kalman filter.

4. The circuit of claim 1, where the processing unit is configured to demodulate the sequence of SS-OCT calibration signal digital values using an interpolated discrete Fourier transform.

5. The circuit of claim 1, where the processing unit is configured to demodulate the sequence of SS-OCT calibration signal digital values using square law envelope detection.

6. The circuit of claim 1, where the level crossing sampler is implemented in the processing unit as one of software, firmware, or hardware logic.

7. The circuit of claim 1, comprising a digital to analog converter (DAC) coupled to an output of the processing unit that is configured to convert the sequence of wave number digital values to an analog wave number signal, where the level crossing sampler processes the analog wave number signal to generate the SS-OCT calibration clock pulse.

8. The circuit of claim 7, where the level crossing sampler comprises an operational amplifier and a comparator, where a positive input of the operational amplifier is coupled to an output of the DAC, a negative input of the operational amplifier is coupled to a source of a varying level reference, and an output of the operational amplifier is coupled to an input of the comparator.

9. The circuit of claim 8, where the level crossing sampler comprises an asynchronous accumulator and a second ADC, where an output of the comparator is coupled to a clock input of the asynchronous accumulator, an output of the asynchronous accumulator is coupled to an input of the second ADC, and an output of the second ADC is coupled to the negative input of the operational amplifier.

10. A method of generating a swept source optical coherence tomography (SS-OCT) imaging calibration clock, comprising:
    converting an SS-OCT optical calibration signal by a photodetector to an SS-OCT electrical calibration signal;
    converting the SS-OCT electrical calibration signal by an analog-to-digital converter (ADC) to a sequence of SS-OCT calibration signal digital values;
    demodulating the sequence of SS-OCT calibration digital values by a processing unit to obtain a sequence of SS-OCT wave number digital values, where each SS-OCT wave number digital value corresponds to one of the SS-OCT calibration signal digital values; and
    in response to the SS-OCT wave number digital value matching one of a plurality of predefined SS-OCT wave number digital values, generating an SS-OCT calibration clock pulse, whereby an SS-OCT interferometric optical signal is sampled based on the SS-OCT calibration clock pulse.

11. The method of claim 10, where demodulating the sequence of SS-OCT calibration digital values comprises Kalman filtering the sequence of SS-OCT calibration digital values by the processing unit.

12. The method of claim 10, where demodulating the sequence of SS-OCT calibration digital values comprises performing an interpolated discrete Fourier transform on the sequence of SS-OCT calibration digital values by the processing unit.

13. The method of claim 10, where demodulating the sequence of SS-OCT calibration digital values comprises performing square law envelope detection on the sequence of SS-OCT calibration digital values by the processing unit.

14. A circuit for generating a swept source optical coherence tomography (SS-OCT) imaging calibration clock, comprising:
    a first photodetector configured to convert an SS-OCT optical calibration signal to an SS-OCT electrical calibration signal;
    a first analog-to-digital converter (ADC) coupled to the first photodetector and configured to convert the SS-OCT electrical calibration signal to a sequence of SS-OCT calibration signal digital values;
    a processing unit coupled to the first ADC that, when initiated, is configured to demodulate the sequence of SS-OCT calibration signal digital values to obtain a sequence of SS-OCT wave number digital values, where each SS-OCT wave number digital value corresponds to one of the SS-OCT calibration signal digital values;
    a level crossing sampler that is configured to track a wave number associated with the SS-OCT optical calibration signal and to generate an SS-OCT calibration clock pulse;
    a second photodetector configured to convert an SS-OCT optical interferometric signal to an SS-OCT electrical interferometric signal;
    a second ADC coupled to the second photodetector and coupled to receive the SS-OCT calibration clock pulse and configured to sample the SS-OCT electrical interferometric signal in response to the SS-OCT calibration clock pulse and to convert the sample to a SS-OCT interferometric signal digital value, where the processing unit is further configured to process a plurality of SS-OCT interferometric signal digital values to a light reflection coefficient value associated with a point on an imaging target.

15. The circuit of claim 14, where the circuit is an integrated circuit.

16. The circuit of claim 14, where the first photodetector and the second photodetector are InGaAs photodiodes.

17. The circuit of claim 14, comprising an asynchronous to synchronous converter coupled to receive the SS-OCT interferometric signal digital values from the second ADC asynchronously and coupled to provide the SS-OCT interferometric signal digital values synchronously to the processing unit.

18. The circuit of claim 14, where the processing unit is configured to demodulate the sequence of SS-OCT calibration signal digital values using a Kalman filter.

19. The circuit of claim 14, where the processing unit is configured to demodulate the sequence of SS-OCT calibration signal digital values using an interpolated discrete Fourier transform.

20. The circuit of claim 14, where the processing unit is configured to demodulate the sequence of SS-OCT calibration signal digital values using square law envelope detection.

* * * * *